US006607476B1

(12) United States Patent
Barnhart

(10) Patent No.: US 6,607,476 B1
(45) Date of Patent: Aug. 19, 2003

(54) BRACHYTHERAPY POSITIONING SYSTEM

(75) Inventor: William H. Barnhart, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 09/271,176

(22) Filed: Mar. 17, 1999

Related U.S. Application Data

(60) Provisional application No. 60/102,634, filed on Oct. 1, 1998.

(51) Int. Cl.[7] ............................................. A61M 25/10
(52) U.S. Cl. ........................................................ 600/3
(58) Field of Search .......................... 600/1–8; 604/102, 604/108, 95–97, 160, 194, 198, 22, 28; 606/8, 159, 191, 194–198, 200

(56) References Cited

U.S. PATENT DOCUMENTS

| | | | |
|---|---|---|---|
| 5,199,939 A | | 4/1993 | Dake et al. |
| 5,213,561 A | | 5/1993 | Weinstein et al. |
| 5,302,168 A | | 4/1994 | Hess |
| 5,411,466 A | | 5/1995 | Hess |
| 5,484,384 A | | 1/1996 | Fearnot |
| 5,540,659 A | | 7/1996 | Teirstein |
| 5,643,171 A | * | 7/1997 | Bradshaw et al. ............. 600/1 |
| 5,713,828 A | | 2/1998 | Coniglione |
| 5,730,698 A | * | 3/1998 | Fischell et al. ................. 600/3 |
| 5,938,582 A | * | 8/1999 | Ciamacco, Jr. et al. ......... 600/3 |
| 5,976,106 A | * | 11/1999 | Verin et al. ..................... 600/3 |
| 6,013,019 A | * | 1/2000 | Fischell et al. ................. 600/3 |
| 6,074,339 A | * | 6/2000 | Gambale et al. ............... 600/3 |
| 6,159,139 A | * | 12/2000 | Chiu .............................. 600/3 |
| 6,267,775 B1 | * | 7/2001 | Clerc et al. .................... 600/3 |

FOREIGN PATENT DOCUMENTS

| | | | | |
|---|---|---|---|---|
| EP | 813894 | * | 12/1997 | ..................... 600/3 |
| EP | 865803 | * | 9/1998 | ..................... 600/3 |

* cited by examiner

*Primary Examiner*—Samuel G. Gilbert
(74) *Attorney, Agent, or Firm*—Woodard, Emhardt, Moriarty, McNett & Henry LLP

(57) ABSTRACT

A brachytherapy positioning apparatus and a method of positioning a radiation source within a passageway of a patient's body are disclosed. The apparatus is configured to position a radioactive source in the center of the passageway being treated so that all regions of the passageway wall receive the same dosage of radiation. The brachytherapy positioning apparatus may include an elongated member, a distal end cap, a reconfigurable positioning element, and a control member. The positioning element may be positioned between the distal end cap and the elongated member about a portion of the control member and may be selectively changed between a radially expanded state and a retracted state with the control member. In one embodiment, the positioning element includes a plurality of generally parallel wires that each expand and retract along a different radius originating from a centerline axis of the control member.

30 Claims, 6 Drawing Sheets

BRACHYTHERAPY POSITIONING SYSTEM

CROSS REFERENCE TO RELATED APPLICATIONS

The present invention claims the benefit of U.S. Provisional Patent Application Ser. No. 60/102,634, filed Oct. 1, 1998.

FIELD OF THE INVENTION

The present invention relates to techniques for delivering a medical treatment material to a site along an internal passageway of a patient's body, and more particularly, but not exclusively, relates to brachytherapy positioning systems and methods.

BACKGROUND OF THE INVENTION

Brachytherapy is a form of radiation therapy whereby a radiation source is placed in or near target cells, typically malignant cells. Brachytherapy has also been employed to prevent restenosis in vascular passageways after angioplasty treatment. Due to the fact that the intensity of radiation that emanates from a source varies inversely with the square of the radial distance from the source, when treatment is administered in vascular passageways, the source of radiation must be properly positioned. If the radiation source is not centered properly, the walls of the vessel being treated will not receive a uniform dosage of radiation; certain portions of the wall will receive too much radiation and other portions will receive too little radiation.

One scheme utilizes a balloon catheter to deliver the radiation source and centers the source by inflating the balloon. When utilized in vascular passageways, such devices can potentially impede or stop blood flow during treatment. Blocking blood flow can lead to several complications. For example, impeding blood flow in a coronary artery for a prolonged period of time may result in myocardial infarction, angina, or ischemia. A brachytherapy positioning system is therefore needed that reduces blood flow obstruction during treatment. The present invention addresses this need, and has other benefits and advantages.

SUMMARY OF THE INVENTION

The present invention relates to a brachytherapy positioning apparatus and a method for positioning a medical treatment material.

One form of the present invention is a unique brachytherapy apparatus. This apparatus may include a reconfigurable positioning element through which blood may flow when in an expanded state. Additionally or alternatively, another form of the present invention includes a unique medical treatment method. This unique method may include utilization of a brachytherapy apparatus according to the present invention to deliver and position a radiation source at a predetermined location along a passageway in a patient's body.

It is therefore an object of the invention to provide a unique brachytherapy positioning apparatus.

It is a further object of the present invention to provide a unique method of positioning a medical treatment material within a patient's body.

These and other objects, forms, embodiments, features, aspects, benefits, and advantages of the invention will become apparent from the drawings and following detailed description.

DESCRIPTION OF THE PREFERRED EMBODIMENTS

Figure 1:
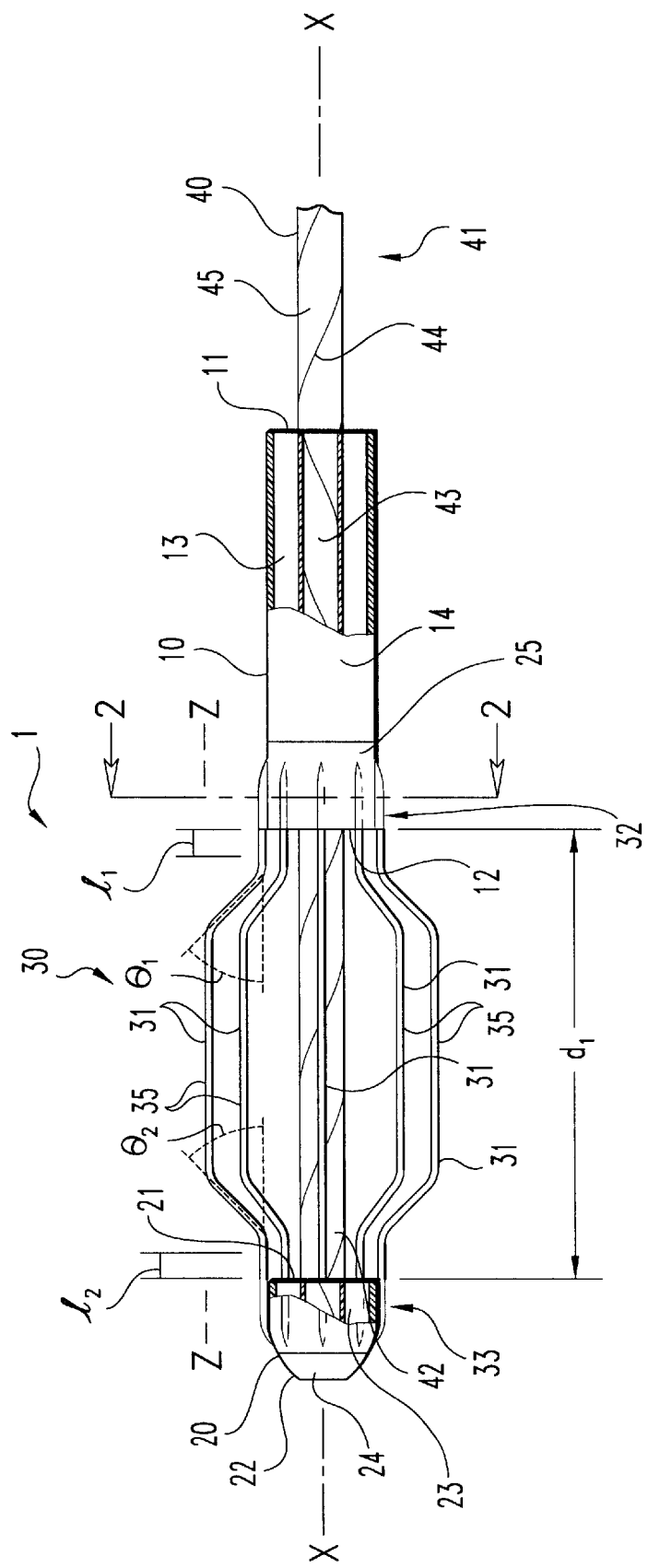
FIG. 1 is a partial, cut away side view of a first embodiment of a brachytherapy apparatus of the present invention having a positioning element 30 in an expanded state.

For the purposes of promoting an understanding of the principles of the invention, reference will now be made to various preferred embodiments and specific language will be used to describe the same. It will nevertheless be understood that no limitation of the scope of the invention is thereby intended. Any alterations and further modifications of the embodiments, and any further applications of the principles of the invention as illustrated herein are contemplated as would normally occur to one skilled in the art to which the invention relates.

As described above, the present invention relates to a brachytherapy positioning apparatus and a method of positioning a medical treatment material, such as a radiation source, in a passageway of a patient's body. In one preferred embodiment, the apparatus generally centers a radiation source in the passageway, such that all points along the wall of the passageway being treated will receive substantially the same dose of radiation. While the apparatus is partially suited to use in vascular vessels, such as coronary arteries and veins, carotid arteries and veins, and renal arteries and veins; it may be utilized in any other passageways of the body as well.

Referring to FIGS. 1–4, one embodiment of brachytherapy positioning apparatus 1 is shown. Apparatus 1 is comprised of an elongated member 10, a distal end cap 20, an expandable/retractable positioning element 30, and a control member 40. Elongated member 10 and distal end cap 20 are spaced apart from each other along longitudinal centerline axis XX of apparatus 1, with element 30 extending from elongated member 10 to distal end cap 20. Elongated member 10 includes proximal end portion 11, distal end portion 12 and a lumen 13 extending therethrough. Elongated member 10 may be a catheter having an outside and inside diameter determined by the diameter of the passageway being treated. In one nonlimiting example, typical dimensions of elongated member 10 for use in certain cases relating to human coronary artery treatment include an inside diameter of about 0.97 millimeters (mm) (0.038 inches) and an outside diameter of about 1.35 mm (0.053 inches). Elongated member 10 may be made of materials as known in the art, including polytetrafluoroethylene, polyethylene, polyurethane, nylon or a combination thereof, to name a few. The length of elongated member 10 will vary depending on the application. For the previously described coronary artery treatment example, a typical length is about 100 centimeters (cm).

Distal end cap 20 includes a proximal end portion 21, a distal end 22 and a lumen 23 extending at least partially therethrough. As seen in FIG. 1, distal end portion 12 of elongated member 10 opposes proximal end portion 21 of distal end cap 20. Distal end cap 20 is configured for translational movement relative to elongated member 10 to reconfigure element 30. Distal end cap 20 may be a length of catheter having about the same inside and outside diameter as elongated member 10. Distal end cap 20 is typically about 0.076 mm (0.003 inches) in length for the coronary artery example. Distal end cap 20 may be constructed from any of the materials used for elongated member 10. Nonetheless, in other embodiments, distal end cap 20 may have a different size, shape, and/or composition than elongated member 10.

Figure 2:
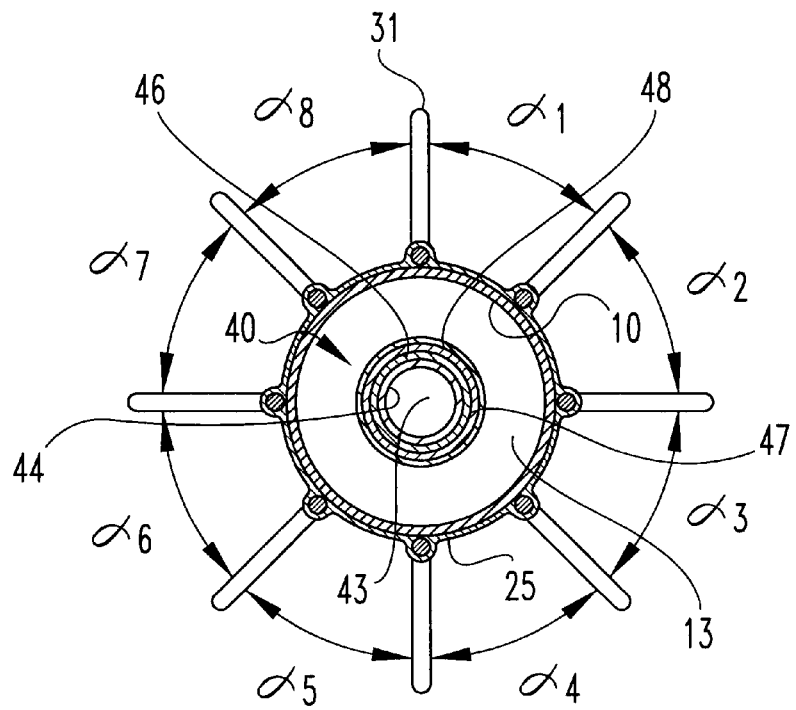
FIG. 2 is a partial sectional view of the brachytherapy apparatus taken along section line 2—2 of FIG. 1.

Element 30 is generally disposed between elongated member 10 and distal end cap 20. Element 30 includes a plurality of wires 31. Preferably, wires 31 number at least six. More preferably, wires 31 number about eight. Each of the wires has a corresponding longitudinal axis ZZ, only one of which is shown in FIG. 1 to preserve clarity. Proximal portion 32 of each of wires 31 is attached to distal end portion 12 of elongated member 10 and distal portion 33 of each of the wires is attached to proximal end 21 of distal end cap 20. Wires 31 may be attached to outer surface 14 of elongated member 10 and outer surface 24 of distal end cap 20 with a medical grade adhesive with the corresponding bond sites being covered with heat shrink tubing 25 as shown in FIG. 2. In other embodiments, a different attachment technique may be utilized as would occur to those skilled in the art. Wires 31 extend along axis XX of apparatus 1 with axis ZZ of each wire 31 being generally parallel to axis XX.

Wires 31 are preferably made of a superelastic/shape memory material such as one selected from the family of nickel-titanium alloys collectively referred to as Nitinol. Shape memory alloys can be formed into a predisposed shape which it will "remember" over a given temperature range even when this shape has been substantially deformed by the application of mechanical force. When this material is within this temperature range, it generally exhibits the property of superelasticity whereby it will allow substantial mechanical deformation to occur in response to external stress, and will still return back to its predisposed shape when the external stress is removed. At temperatures below this range, the material will not entirely regain its predisposed shape on the removal of external stress, but will regain the remainder of its predisposed shape upon heating back within the relevant temperature range. At still lower temperatures, the material will stay deformed after stress on it has been released, but will resume its remembered, predisposed shape when heated back into the appropriate temperature range. Notably, the threshold temperature at which the shape memory/superelastic properties are exhibited may differ depending on whether the material is being heated up or cooled down. For the present invention, the material to be selected for wires 31 is preferably well within its shape memory/superelastic temperature range at the nominal temperature of the human body (about 37° C.).

Apparatus 1 also includes control member 40. Control member 40 operates to retract and expand element 30. Distal end portion 42 of control member 40 is preferably disposed in lumen 23 of distal end cap 20 and is attached to distal end cap 20 at distal end portion 42 by methods known in the art, including use of a medical adhesive, glue, or using other techniques known to those skilled in the art. Control member 40 is preferably a guidewire, such as a Cragg guidewire, having a proximal end portion 41, a distal end portion 42 and a treatment lumen 43 extending therethrough. The Cragg guidewire is comprised of a flat wire spring 44 coated with a layer 46 of Teflon which is in turn coated with a layer 47 of polyimide. The coated wire spring is then covered with heat shrink tubing 48. The thickness of these coatings can vary as one skilled in the art would appreciate. Alternatively, control member 40 may also be any appropriately sized catheter, including a catheter reinforced with braiding. In other embodiments, a different construction or composition of member 40 may be utilized as would occur to those skilled in the art.

For example, in one alternative embodiment, distal end cap 20 is integrally formed as the distally terminating portion of control member 40. For this embodiment, distal end cap may be from the same material as control member 40, with a comparable construction, or may otherwise differ as would occur to one skilled in the art. In some forms of the present invention, apparatus 1 is utilized to provide medical treatment by delivering a radioactive source through lumen 43 of control member 40 to a location adjacent distal end cap 20. For these forms, distal end cap 20 is typically arranged to prevent passage of the radioactive source out of apparatus 1. Such arrangements may include a partial or complete closure of distal end 22 of distal end cap 20 to at least partially obstruct passage of materials into or out of a distal opening of lumen 43. In still other embodiments, such blockage may not be required, or control member 40 may be otherwise shaped or constructed to prevent the unintended passage of materials.

Control member 40 is partially disposed in lumen 13 of elongated member 10. FIGS. 1–4 depict elongated member 10 with a large internal diameter to more clearly distinguish control member 40 from lumen 13. However, it should be appreciated that the internal diameter of elongated member 10 and the outside diameter of control member 40 are preferably chosen such that control member 40 fits snugly in lumen 13. Accordingly, control member 40 is preferably configured to slide through elongated member 10 with each having a substantial amount of its surface area in contact with the other. While the dimensions of control member 40 may vary as needed, for a preferred coronary artery application, control member 40 includes an internal diameter of about 0.027 inches (in) (0.69 mm) and an outside diameter of about 0.038 in (0.97 mm). The length may also vary but is preferably about 150 cm for the coronary artery application. The portion of control member 40 that extends between distal end cap 20 and elongated member 10 is generally surrounded by element 30.

Figure 3:
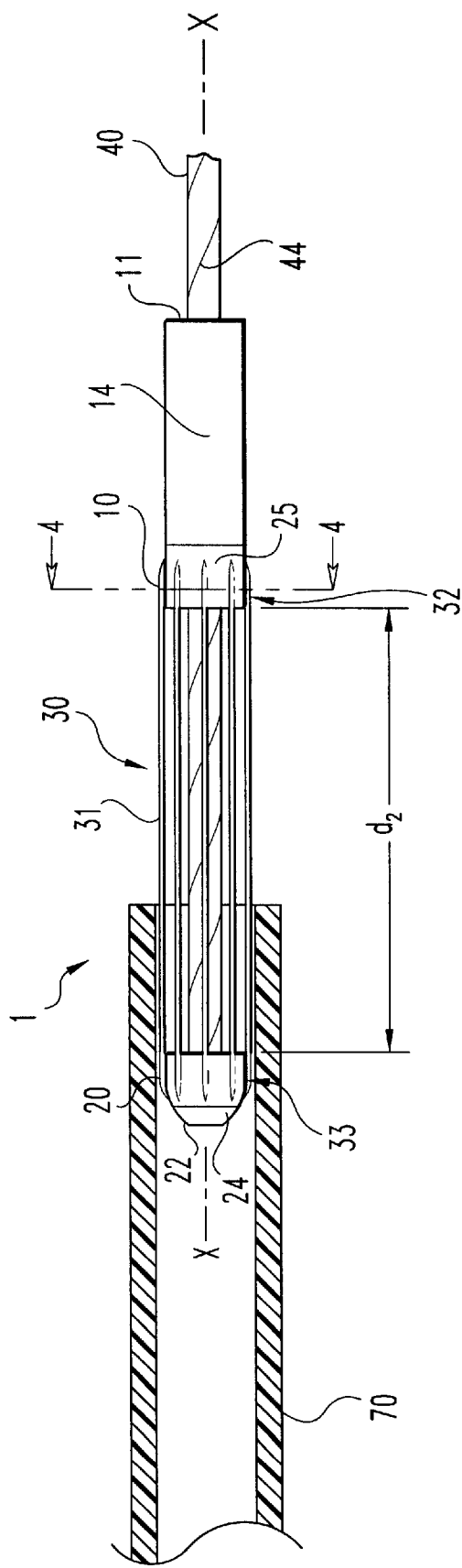
FIG. 3 is a partial side view of the brachytherapy apparatus shown in FIG. 1 with element 30 in a retracted state and partially placed in a guiding catheter shown in section.

Referring generally to FIGS. 1–4, selected operational aspects of apparatus 1 are next described. For example, element. 30 may be reconfigured by control member 40 to aid in the positioning of a medical treatment material within a passageway of a patient's body. This reconfiguration includes selectively reshaping element 30 between a radially retracted state and a radially expanded state. In order to retract element 30, elongated member 10 may be held while force is applied to proximal end 41 of control member 40, such that control member 40 is pushed in a distal direction, which in turn pushes distal end cap 20 away from elongated member 10, increasing the distance therebetween. In order to fully radially retract positioning element 30, control member 40 is pushed distally until proximal end portion 21 of distal end cap 20 and distal end portion 12 of elongated member 10 are separated by second distance $d_2$. When element 30 is in its fully retracted state as shown in FIG. 3, wires 31 of element 30 are substantially straightened along their entire length, each wire 31 has a longitudinal axis that is generally parallel to central longitudinal axis XX of apparatus 1, wires 31 are generally non-overlapping, and wires 31 are generally equidistant from each other along their entire length.

The application of force with control member 40 deforms wires 31, causing them to lengthen along axis XX and radially contracting element 30 about axis XX. However, this force is preferably not sufficient to result in any substantial degree of permanent or "plastic" deformation of wires 31. Instead, it is preferred that when that force exerted on wires 31 is removed, wires 31 substantially return to a predetermined shape existing before the retraction as shown in FIG. 1. As FIG. 1 illustrates, wires 31 each are predisposed to resume an arched shape which collectively result in a radial expansion of element 30 with respect to axis XX.

When positioning element 30 is in its expanded state as shown in FIGS. 1 and 2, central segment 35 of each wire 31 constitutes a majority of its length along axes XX, ZZ, and is preferably substantially straight. Also, it is preferred that wires 31 not overlap each other (i.e., extend independently of each other), along their entire length. Central segments 35 are generally positioned about control member 40 between elongated member 10 and distal end cap 20. Moreover, as wires 31 extend along apparatus 1, longitudinal axis ZZ of each of wires 31 continues to be generally parallel to central longitudinal axis XX of control member 40 where control member 40 extends between elongated member 10 and distal end cap 20.

As seen more clearly in FIG. 1, a length $l_1$ of each wire 31 at proximal end 32 extends substantially straight from elongated member 10 toward distal end cap 20. Preferably, length $l_1$, is no more than about 0.051 mm (0.002 inches). Proceeding in a distal direction, wires 31 at proximal end 32 curve upward at an angle θ then turn again to form a substantially straight central segment 35 for a majority of their length. Wires 31 then curve downward at an angle $θ_2$ prior to becoming generally straight for a length $l_2$ and attaching to distal end cap 20 at distal end 33 of wires 31. Angles $θ_1$, $θ_2$ may vary as one skilled in the art would appreciate. However, angles $θ_1$, $θ_2$ are both preferably about 45°. Also, it is preferred that $l_1$ and $l_2$ be about equal, but $l_1$ and $l_2$ may also vary from one another in alternative embodiments. Wires 31 are preferably about 0.23 mm (0.009 inches) in diameter but may vary in diameter as one skilled in the art would appreciate.

Figure 4:
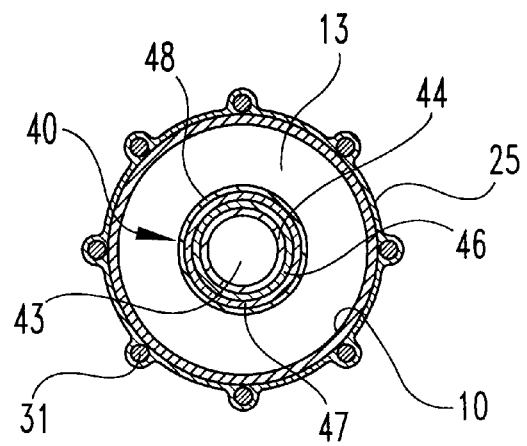
FIG. 4 is a partial sectional view of the brachytherapy apparatus taken along section line 4—4 of FIG. 3.

Element 30 may exist in a radially expanded state as depicted in FIGS. 1 and 2 or in a radially retracted state as depicted in FIGS. 3 and 4. In the expanded state of element 30, wires 31 extend along a first distance $d_1$ between proximal end portion 21 of distal end cap 20 and distal end portion 12 of elongated member 10 (see FIG. 1). In the retracted state of element 30, wires 31 extend along a second distance $d_2$ between proximal end portion 21 of distal end cap 20 and distal end portion 12 of elongated member 10 (see FIG. 2). Second distance $d_2$ is greater than first distance $d_1$ corresponding to the more longitudinally extended condition of element 30 when radially retracted. In one embodiment, first distance $d_1$ is about 30 mm and second distance $d_2$ is about 32 mm. When transitioning between the retracted and expanded states, wires 31 move independent of each other. In other words, movement of one wire 31 in response to an adjustment of control member 40 does not cause movement of another of wires 31. Instead, movement of each wire 31 is caused directly by movement of control member 40 relative to elongated member 10. Moreover, as best seen in the sectional view of apparatus 1 depicted in FIG. 2, each of wires 31 are preferably equidistantly angularly spaced apart from each of their neighboring wires and number about eight. In such an embodiment as depicted in FIG. 2, angles $α_1$–$α_8$ between adjacent wires 31 are each preferably about 45°; however, in other embodiments wires 31 may not be uniformly spaced apart from each other.

Figure 5:
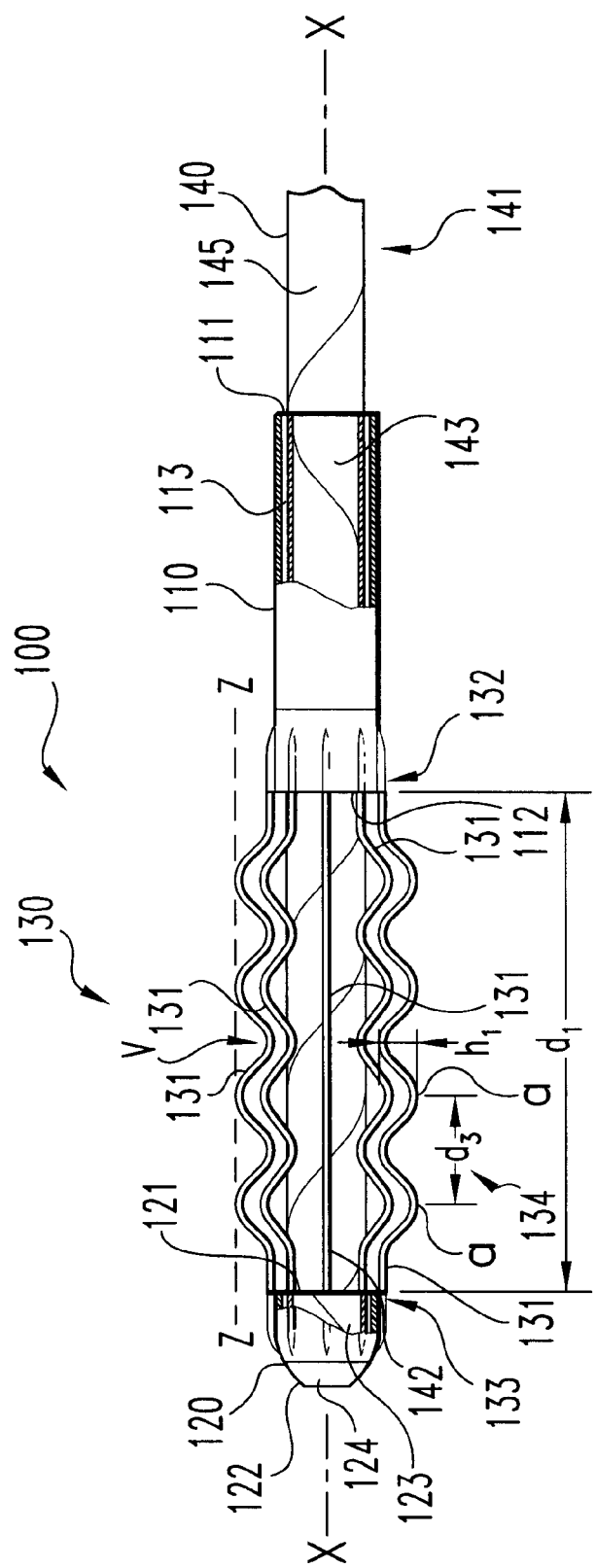
FIG. 5 is a partial, cut away side view of a second embodiment of a brachytherapy positioning apparatus of the present invention having a positioning element 130 in an expanded state.
Figure 6:
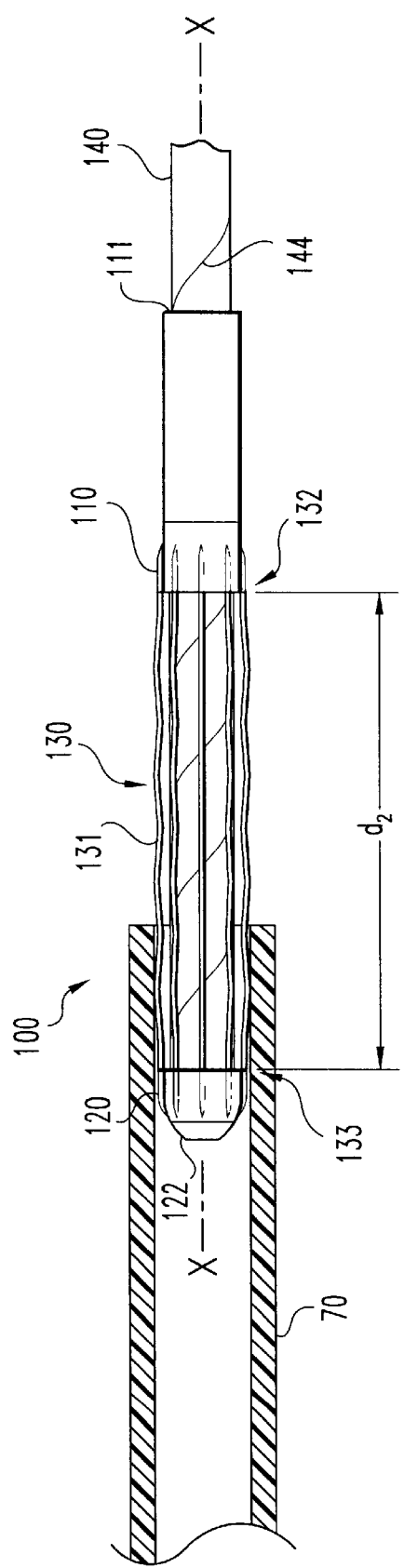
FIG. 6 is a partial side view of the brachytherapy positioning apparatus shown in FIG. 5 with element 130 in a retracted state and partially placed in a guiding catheter shown in section.

FIGS. 5 and 6 show brachytherapy positioning apparatus 100 of another embodiment of the present invention. Apparatus 100 is preferred for various vascular passageways, but, like apparatus 1, may be used in any body lumen or passage as would occur to those skilled in the art. Apparatus 100 includes elongated member 110, distal end cap 120, reconfigurable positioning element 130, and control member 140 arranged relative to each other along axis XX as described for like named constituents of apparatus 1; however, the relative diameters of control member 140 are depicted differently in FIGS. 5 and 6.

Elongated member 100 includes proximal end portion 111, distal end portion 112, and lumen 113 extending therethrough. Distal end cap 120 includes proximal end portion 121, distal end 122, and lumen 123 extending at least partially therethrough. Control member 140 extends through lumen 113 of elongated member 110 and has a proximal end portion 141 opposite distal end portion 142. Distal end portion 142 terminates with distal end cap 120. Control member 140 also preferably defines treatment lumen 143 along its length. Elongated member 110, distal end cap 120, and control member 140 may be constructed and formed from materials like elongated member 10, distal end cap 20, and control member 40 of apparatus 1, respectively. Collectively, control member 140 and distal end cap 120 may be moved together relative to elongated member 110 to reconfigure element 130 in the manner analogous to that described for element 30 of apparatus 1.

Retractable/expandable positioning element 130 of apparatus 100 is comprised of a plurality of wires 131. As seen in FIG. 5, each wire 131 includes a series of undulating arcuate segments 134 that collectively approximate a sinusoidal trace. To enhance clarity, only one representative arcuate segment 134 is specifically designated by reference numeral and its length along axis XX is shown as distance $d_3$. The number of arcuate segments 134 for each wire 131 may vary. Preferably, the number of segments 134 for each wire 131 is in a range of about 2 to about 6. More preferably, the number of segments 134 per wire 131 is about 4. Each arcuate segment 134 is aligned longitudinally with its neighboring arcuate segment 134 along the same wire 131. Arcuate segments 134 may individually or collectively be considered arched shapes. Preferably, wires 131 are made from a superelastic/shape memory material or other resilient material arranged to facilitate radial expansion and retraction of element 130.

Distance $d_3$ between apex "a" of segment 134 and apex "a" of its nearest neighboring segment 134 on the same wire 131, and height $h_1$ of the arcuate segments 134 may vary in accordance with the particular size or application of apparatus 100 and/or its constituent components as would occur to those skilled in the art. For a human coronary artery application, distance $d_3$ is preferably in a range of about 5 mm to about 8 mm, and height $h_1$ is preferably in a range of about 4 mm to about 6 mm.

Element 130 is connected at proximal end portion 132 to distal end portion 112 of elongated member 110, and distal end portion 133 of element 130 is connected to proximal end portion 121 of distal end cap 120. These connections are preferably made in the same manner as for element 30 of apparatus 1 to elongated member 10 and distal end cap 20, respectively. Control member 40 extends through element 130 to be fixedly coupled to distal end cap 120. While it is preferred that distal end cap 120 have the same internal and outside diameters as elongated member 110, its relative size may vary as would occur to one skilled in the art. Also, end cap 120 may be formed as an integral part of control member 140 as discussed in connection with end cap 20 and control member 40 of apparatus 1. Apparatus 100 operates to radially expand and retract element 130 in response to the movement of control member 140 through lumen 113 relative to elongated member 110. FIG. 5 depicts element 130 in the expanded state and FIG. 6 depicts element 130 in the retracted state. When transitioning positioning element 130 between retracted and expanded states, wires 131 move independent of one another as in the case of wires 31. Also, when positioning element 130 is retracted, wires 131 are at least partially straightened and each have a longitudinal axis ZZ that is generally parallel to the centerline axis XX where it extends along central member 140 between elongated member. 110 and distal end cap 120.

Figure 7:
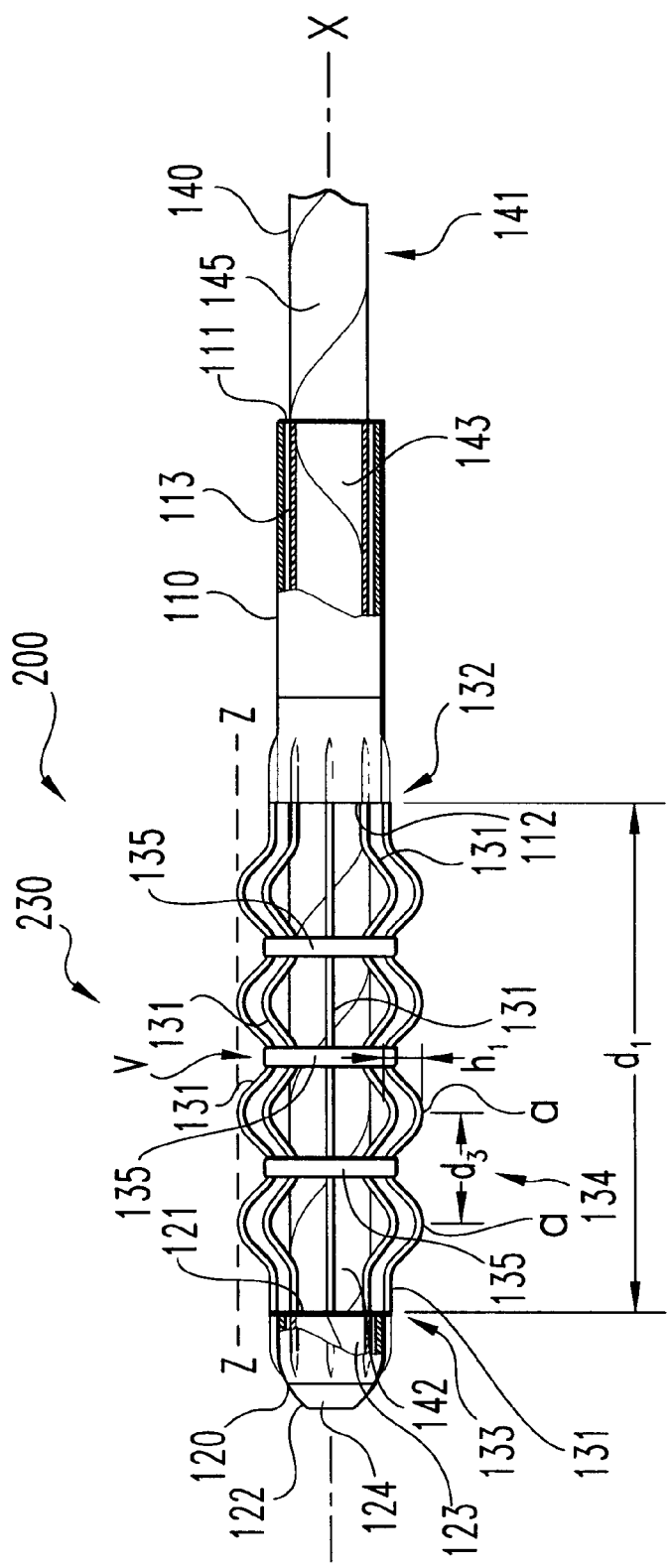
FIG. 7 is a partial, cut away side view of a brachytherapy apparatus of a third embodiment of the present invention.

FIG. 7 depicts brachytherapy positioning apparatus 200 of yet another embodiment of the present invention; where like reference numerals refer to like features previously described. Apparatus 200 includes reconfigurable expansion element 230 with bands 135 disposed around wires 131 in region V, where wires 131 come closest to surface 145 of control member 140 between arcuate segments 134. Bands 135 generally assist in stabilizing wires 131 and generally enhance the ability to position with control member 140. Bands 135 may be composed of any material that would occur to those skilled in the art including metal or plastic, but are preferably composed of a suture material, such as nylon. The bands may be secured to wires 131 with a medical glue, tape, or using techniques as are known to those skilled in the art.

Apparatus 200 operates to provide for the radial expansion and retraction of element 230 by moving control member 140 relative to elongated member 110 in generally the same manner as described for apparatus 1 and apparatus 100. FIG. 7 shows element 230 in an expanded state. Bands 135 are carried by wires 131 and move therewith as element 230 transitions between expanded and retracted conditions.

Referring generally to FIGS. 1–7, in an alternative embodiment, wires 31, 131 of apparatus 1, 100, 200 may be made from a resilient material other than a superelastic/shape memory type. Such alternative materials are selected to behave in a manner sufficient to facilitate the retraction/expansion of element 30, 130, 230, but may not be superelastic or have a temperature dependent shape memory. For example, wires 31, 131 may be formed with coil springs at selected bend points to provide an element resiliency sufficient to assume a predisposed shape for the radially expanded state after being elastically deformed in the radially retracted state. Stainless steel could be used for this alternative embodiment. In other embodiments of the present invention, wires 31, 131 are formed from one or more other types of material or arranged in such other manner as would occur to those skilled in the art. Moreover, elements 30, 130, 230 may alternatively or additionally be formed from constituents other than wires with a generally circular cross section such as helical coils or generally flat strips, to name a few.

Additionally or alternatively, another aspect of the invention is a method of positioning medical treatment material at a predetermined site along a passageway in a patient's body. This method includes providing an apparatus for positioning the treatment material, such as apparatus 1, 100, 200. Prior to advancing apparatus 1, 100, 200 to the predetermined treatment site, positioning element 30, 130, 230 is placed in a retracted state as described above. The element 30, 130, 230 is preferably sized in its retracted state so that it may readily pass through the selected body passageway. The apparatus may then be inserted distal end first, into the proximal end of guiding catheter 70 as shown in FIGS. 3 and 6. Guiding catheter 70 be placed in the passageway with its distal end adjacent the predetermined site within the patient's body prior to insertion of apparatus 1, 100, 200 to assist in directing apparatus 1, 100, 200 to the predetermined site. FIGS. 3 and 6 illustrate elements 30, 130 as they are being placed in a guiding catheter 70 (shown in partial section). Element 230 and apparatus 200 may likewise be inserted in catheter 70. Guiding catheter 70 is preferably sized and arranged to maintain element 30, 130, 230 in its retracted condition, possibly resulting in a certain amount of resistance as apparatus 1, 100, 200 is advanced along guiding catheter 70.

Apparatus 1, 100, 200 may include a radiopaque material to assist in placing it radiographically. After traveling through catheter 70, apparatus 1, 100, 200 is then pushed out of the distal end of the guiding catheter 70 by pushing on apparatus 1, 100, 200 in a distal direction until the resistance decreases. Control member 40, 140 may then be released to radially expand element 30, 130, 230 to its expanded state. Proper positioning of apparatus 1, 100, 200 may be verified by fluorographic or radiographic methods as known in the art. Alternatively, depending on the location of the predetermined site, apparatus 1, 100, 200 may be placed directly in the body lumen of interest while maintaining element 30, 130, 230 in its retracted state with continued application of force to control member 40, 140. This alternative technique may not utilize a guiding catheter.

Once apparatus 1, 100, 200 is positioned, the medical treatment material may be disposed in the treatment lumen 43, 143 of the control member 40, 140 and positioned such that it will be located in the area of the treatment lumen between the elongated member 10, 110 and the distal end cap 20, 120 defined by distance $d_1$. Preferably, element 30, 130, 230 is sized in its expanded state to engage one or more surfaces surrounding the body passageway with corresponding wires 31, 131 to maintain a desired position of control member 40, 140 relative to the passageway. More preferably, element 30, 130, 230 is arranged in its expanded state to generally center control member 40, 140 at the distal end region of the corresponding apparatus 1, 100, 200 to facilitate more uniform application of the treatment.

In a more preferred embodiment, the medical treatment material is a radioactive source that is positioned at the treatment site through treatment lumen 43, 143 of control member 40, 140, respectively. In this more preferred embodiment, the radioactive source is left at the predetermined position for a therapeutically effective period of time as known in the art. When a radioactive source is utilized, it may include one or more radioactive materials known in the art, such as cobalt-60, cesium-137, iridium-192, iodine-125, palladium-103, tantalum-73, tungsten-74 and gold-198, to name a few. Once treatment is completed, the treating material is typically removed by withdrawing it through lumen 43, 143 as appropriate. Apparatus 1, 100, 200 may likewise be withdrawn through the guiding catheter by first pushing on control member 40, 140 to return positioning element 30, 130, 230 to its retracted state, and then withdrawing apparatus 1, 100, 200. When an appropriately sized guiding catheter is utilized, element 30, 130, 230 is maintained in its retracted state once within the guiding catheter 70 for the withdrawal stage. Apparatus 1, 100, 200 may then be pulled through the guiding catheter until it is removed from the patient's body. The guiding catheter 70 may then be removed, (if used).

Other examples of the present invention include a brachytherapy positioning apparatus that comprises an elongated member, a distal end cap, a reconfigurable positioning element, and a control member. The proximal end of the distal end cap and the distal end of the elongated member oppose each other. The positioning element is disposed about a distal portion of the control member and between the distal end cap and the elongated member. The proximal end of the positioning element is attached to the elongated member and the distal end of the positioning element is attached to the distal end cap. The control member extends through the elongated member and the positioning element to adjust position of the distal end cap relative to the elongated member. By adjusting this position, the degree of the expansion of the positioning element is correspondingly controlled.

In a further embodiment of the present invention, this reconfigurable positioning element is in a radially expanded state when the distal end cap and the elongated member are separated by a first distance and in a radially retracted state when the distal end cap and the elongated member are separated by a second distance. The second distance is greater than the first distance. For this form, the positioning element may be placed in the retracted state by applying a force to the control member to push it in a distal direction which moves the distal end cap away from the elongated member. When this force is removed, the control member is released, travelling in a proximal direction in response to a biasing force provided by the positioning element, which also causes it to expand radially.

Yet another embodiment includes an elongated member defining a lumen and extending therethrough and a control member extending through this lumen that terminates with an end cap. The end cap is distally spaced apart from the elongated ember. The control member and thee end cap may be moved together relative to the elongated member. A positioning element is also included that has a number of wires each extending from the elongated member to the end cap. These wires are spaced about a centerline axis of the control member and are each predisposed with an arched shaped. The positioning element is placed in a radially retracted state by applying a force with the control member to push the end cap away from the elongated member. The wires are each at least partially straightened with a longitudinal axis generally parallel to the centerline axis when the positioning element is in the retracted state. The wires each generally return to the predisposed shape to provide a radially expanded state of the positioning element upon removal of the force to position the apparatus.

In still another embodiment, the positioning element includes at least six wires extending from elongated member to the ends cap. For this embodiment, the wires may or may not each have a longitudinal axis generally parallel to the centerline axis when the positioning element is in the radially retracted state. However, the wires are each operable to move independent of one another when transitioning between the retracted state and the expanded state.

Still another embodiment of the present invention includes advancing an apparatus through a passageway in a patient's body to a treatment site. The apparatus includes a positioning element. A force is applied to the apparatus to put the positioning element in a retracted state. This element includes a plurality of wires each under tension with a longitudinal axis generally parallel to a centerline axis of the apparatus while the force is applied. The force is removed after the apparatus reaches the treatment site to establish an expanded state of the positioning element. The wires each assume a predisposed shape in response to the removal of the force to engage a surface surrounding the passageway and positioning the apparatus. A radiation source is delivered with the apparatus to treat the treatment site after the force is removed.

Another alternative embodiment includes providing an apparatus that has a control member extending through an elongated member and a positioning element. The control member terminates with an end cap positioned distal to the elongated member. The positioning element includes a plurality of wires extending from the elongated member to the end cap. This form also includes establishing a retracted state of the element by applying a force with the control member and advancing the apparatus through a passageway of a patient's body to a treatment site. The apparatus is positioned relative to the passageway by releasing the control member to establish a radially expanded state of the positioning element. The wires each radially extend from the control member in the expanded state a greater distance than the retracted state to engage a surface surrounding the passageway. The wires each move independent of one another when transitioning from the retracted state to the expanded state. Also included is delivery of a radiation source with the apparatus to treat the treatment site after positioning.

In still a further embodiment, a brachytherapy positioning apparatus includes an elongated member with a lumen and a distal end cap opposing a distal end of the elongated member. A positioning element is also included that is positioned between the elongated member and the distal end cap and correspondingly attached to each. The positioning element includes a plurality of wires each extending longitudinally along the apparatus. A control member is configured to contact the distal end cap and control radial expansion and retraction of the positioning element. A longitudinal axis of each of the wires extends generally parallel to a centerline axis of the control member between the elongated member and the distal end cap. The wires may be generally straight when the expansion element is in a radially contracted configuration and the wires may include a number of arcuate segments when the expansion element is in a radially expanded configuration.

Commonly owned U.S. Provisional Patent Application Serial No. 60/162,634, filed Oct. 1, 1998, the benefit of which is claimed herein, is hereby incorporated by reference in its entirety. Further, all publications, patents, and patent applications cited in this specification are herein incorporated by reference as if each individual publication, patent, or patent application were specifically and individually indicated to be incorporated by reference and set forth in its entirety herein.

While the invention has been illustrated and described in detail in the drawings and foregoing description, the same is to be considered as illustrative and not restrictive in character, it being understood that only the preferred embodiments have been described and that all changes, equivalents, and modifications that come within the spirit of the invention as defined by the following claims are desired to be protected.

What is claimed is:

1. An apparatus, comprising:

an elongated member defining a lumen extending therethrough;

a control member extending through said lumen and terminating with an end cap, said end cap being distally spaced apart from said elongated member, said control member and said end cap being movable relative to said elongated member;

a positioning element including a plurality of wires each extending from said elongated member to said end cap, said wires being spaced about a centerline axis of said control member and each being predisposed with an arched shape; and wherein said positioning element is placed in a radially retracted state by applying a force with said control member to push said end cap away from said elongated member, said wires are each at least partially straightened with a longitudinal axis generally parallel to said centerline axis when said positioning element is in said retracted state, and said wires each generally return to said predisposed shape to provide a radially expanded state of said positioning element upon removal of said force to position the apparatus.

2. The apparatus of claim 1, wherein said wires number at least 8 and are generally evenly spaced about a circumference of said control member.

3. The apparatus of claim 1, wherein said wires are each made of a shape memory material.

4. The apparatus of claim 1, wherein said control member has a treatment lumen extending therethrough configured to receive a radiation source.

5. The apparatus of claim 1, wherein said arched shape of each of said wires includes a generally straight central segment.

6. The apparatus of claim 1, wherein said arched shape of each of said wires includes a plurality of arcuate segments.

7. The apparatus of claim 6, wherein said apparatus includes a band disposed about said wires in a region between said distal end cap and said elongated member.

8. The apparatus of claim 1, wherein:

said wires number at least 8 and are generally evenly spaced about said control member, and said wires are each made of an alloy including nickel and titanium and move independent of one another when transitioning between said retracted state and said expanded state;

said control member has a treatment lumen extending therethrough configured to receive a radiation source; and said end cap is closer to said elongated member when said positioning element is in said expanded state than when said positioning element is in said retracted state.

9. An apparatus, comprising:

an elongated member defining a lumen therethrough, said elongated member being configured for placement in a passageway in a patient's body;

a control member disposed in said lumen of said elongated member and terminating with an end cap, said end cap being spaced apart from said elongated member, said control member and said end cap being arranged to be selectively positioned relative to said elongated member;

a positioning element including at least six wires extending from said elongated member to said end cap; and wherein said positioning element is placed in a radially retracted state by applying a force with said control member to push said end cap away from said elongated member, and said wires each generally assume an arched shape to provide a radially expanded state of said positioning element relative to a centerline axis of said control member upon removal of said force, said wires each being operable to move independent of one another when transitioning between said retracted state and said expanded state.

10. The apparatus of claim 9, wherein said wires number 8 and are generally evenly spaced about said control member.

11. The apparatus of claim 9, wherein said wires are comprised of a shape memory material and are each predisposed to assume said arched shape.

12. The apparatus of claim 9, wherein each of said wires includes at least 3 arcuate segments.

13. The apparatus of claim 12, further comprising a number of bands disposed about said wires in a region between said end cap and said elongated member.

14. The apparatus of claim 9, wherein said wires each include a generally straight central segment when said positioning element is in said expanded state.

15. The apparatus of claim 9, wherein said control member has a treatment lumen extending therethrough configured to receive a radiation source.

16. A method, comprising:

advancing an apparatus having a positioning element through a passageway of a patient's body to a treatment site, the positioning element being in a retracted state during said advancing and including a plurality of wires each under tension with a longitudinal axis generally parallel to a centerline axis of the apparatus during said advancing;

expanding the positioning element after reaching the treatment site, the wires each assuming a predisposed shape during said expanding in response to removal of a force applied to the wires with the apparatus, the wires each engaging a surface surrounding the passageway to position the apparatus during said expanding; and delivering a radiation source with the apparatus to treat the treatment site after said expanding.

17. The method of claim 16, wherein the apparatus includes a guiding catheter, an elongated member extending through the guiding catheter, and a control member extending through the elongated member, a proximal end of the positioning element being coupled to the elongated member and a distal end of the positioning element being coupled to the control member, the wires being positioned about the control member.

18. The method of claim 16, further comprising retracting the positioning element by reapplying the force to the wires with the apparatus and withdrawing the apparatus through the passageway after said delivering.

19. The method of claim 16, wherein said delivering includes advancing the radiation source through a lumen defined by the apparatus.

20. The method of claim 16, wherein the apparatus includes a control member extending through an elongated member, the control member having a distal end portion extending further away from the elongated member when the positioning element is in the retracted state during said advancing than when the positioning element is in an expanded state during said expanding.

21. The method of claim 16, wherein said expanding includes moving the wires independent of one another to transition from the retracted state to an expanded state.

22. The method of claim 16, wherein the predisposed shape of each of the wires is generally arched and includes a generally straight central segment.

23. The method of claim 16, wherein the predisposed shape of each of the wires is generally arched and includes a plurality of arcuate segments.

24. The method of claim 16, wherein the radiation source is generally centered in the passageway by the wires when the positioning element is in the expanded state.

25. A method, comprising:

providing an apparatus including a control member extending through an elongated member, and a positioning element, the control member terminating with an end cap positioned distal to the elongated member, the positioning element including a plurality of wires extending from the elongated member to the end cap;

establishing a radially retracted state of the positioning element by applying a force with the control member to push the end cap away from the elongated member;

advancing the apparatus through a passageway of a patient's body to a treatment site;

positioning the apparatus relative to the passageway by releasing the control member to establish a radially expanded state of the positioning element, the wires each radially extending away from the control member in the expanded state a greater distance than in the retracted state to engage a surface surrounding the passageway, the wires each moving independent of one another when transitioning from the retracted state to the expanded state; and delivering a radiation source with the apparatus to treat the treatment site after said positioning.

26. The method of claim 25, further comprising withdrawing the apparatus through the passageway after treating the treatment site with the radiation source for a predetermined amount of time.

27. The method of claim 25, wherein said delivering includes advancing the radiation source through a lumen defined by the apparatus.

28. The method of claim 25, wherein the wires each assume a predisposed arched shape in the expanded state that includes a generally straight central segment.

29. The method of claim 25, wherein the wires each assume a predisposed arched shape in the expanded state that includes a plurality of arcuate segments.

30. The method of claim 25, wherein the radiation source is generally centered in the passageway by the wires when the positioning element is in the expanded state.

* * * * *